(12) United States Patent
Jaeger

(10) Patent No.: US 6,564,620 B1
(45) Date of Patent: May 20, 2003

(54) VISUALLY INDICATING CORROSION SENSING

(75) Inventor: Paul Jaeger, St. Paul, MN (US)

(73) Assignee: Conditions Incorporated, St. Paul, MN (US)

( * ) Notice: Subject to any disclaimer, the term of this patent is extended or adjusted under 35 U.S.C. 154(b) by 0 days.

(21) Appl. No.: 09/342,616

(22) Filed: Jun. 29, 1999

Related U.S. Application Data

(60) Provisional application No. 60/090,981, filed on Jun. 29, 1998.

(51) Int. Cl.$^7$ ............... G01N 17/00; G01N 15/00
(52) U.S. Cl. ................................. 73/86; 73/866.5
(58) Field of Search ................ 73/86, 866.5; 324/700

(56) References Cited

U.S. PATENT DOCUMENTS

| | | | |
|---|---|---|---|
| 4,006,414 A | | 2/1977 | Parker .................. 324/106 |
| 4,019,133 A | * | 4/1977 | Manley et al. ......... 324/65 CR |
| 4,217,544 A | * | 8/1980 | Schmidt ............... 324/65 CR |
| 4,225,216 A | | 9/1980 | Boyd et al. ............ 350/357 |
| 4,280,124 A | * | 7/1981 | Wuertele ............... 340/650 |
| 4,388,166 A | * | 6/1983 | Suzuki et al. .......... 204/403 |
| 4,823,625 A | * | 4/1989 | Hamilton .............. 73/866.5 |
| 4,909,091 A | * | 3/1990 | Ellmann et al. ........ 73/866.5 |

OTHER PUBLICATIONS

Forslund, M., et al., "A Quartz Crystal Microbalance Probe Developed for Outdoor In Situ Atmospheric Corrosivity Monitoring", *J. Electrochem.Soc., 143*, The Electrochemical Society, Inc., 839–844, (Mar. 1996).

Lee, W., et al., "A Comparison of the Mass and Resistance Change Techniques for Investigating Thin Film Corrosion Kinetics", *J. Electrochem. Soc.: Solid–State Science and Technology, 124*, 1744–1747, (Nov. 1977).

Pacheco, A., et al., "The Outdoor Performance Of Printed –Circuit Iron Cells In Self–Driven Operation: Electrochemical and Environmental Features", *Corrosion Science, 40*, Published by Elsevier Science Ltd., 603–618, (1998).

Roller, D., et al., "Development of Thin Metal Film Corrosion Indicators", *Corrosion–National Association of Corrosion Engineers, 16*, 105–110, (Aug. 1960).

Tullmin, M., et al., "Prediction Of Aircraft Corrosion Damage—Atmospheric Parameters and Corrosivity Sensors", *Corrosion 98, Paper No. 606*, 1–14, (1998).

Vassie, P.R., et al., "Electrode Potentials For On–Site Monitoring Of Atmospheric Corrosion Of Steel", *Corrosion Science, 25*, Pergamon Press Ltd., 1–13, (1985).

Veselyi, S., et al., "Testing Of Sensors For Atmospheric Corrosion", *Corrosion 98, Paper No. 342*, 1998 by NACE International, 1–9, (1998).

\* cited by examiner

*Primary Examiner*—Daniel S. Larkin
*Assistant Examiner*—Katrina Wilson
(74) *Attorney, Agent, or Firm*—Schwegman, Lundberg, Woessner & Kluth, P.A.

(57) ABSTRACT

Corrosion sensors and methods of their use for monitoring corrosion of a material of interest. The corrosion sensors are adapted to be placed in the environment containing the material of interest during the period when corrosion is taking place. The corrosion sensors include a power source, a visual indicator and an electrode contained on a support. Changes in the electrical resistance of the electrode facilitate a display on the visual indicator including changes in color or brightness. Some corrosion sensors have power sources activated by directing a light source or other electromagnetic radiation source at the corrosion sensor. Some corrosion sensors have visual indicators containing thermochromic or electrochromic materials that are responsive to changes in voltage drop or current flow across the visual indicator. Some corrosion sensors have tracking devices to provide tracking information about the corrosion sensor. Some corrosion sensors have proximity sensors to inhibit the display on the visual indicator when not in proximity of a trigger.

18 Claims, 4 Drawing Sheets

VISUALLY INDICATING CORROSION SENSING

CROSS-REFERENCE TO RELATED APPLICATION

This application is a continuation-in-part of U.S. provisional application No. 60/090,981, filed Jun. 29, 1998, and incorporated herein by reference.

TECHNICAL FIELD

The present invention relates generally to corrosion sensing and in particular to methods and apparatus for providing visual display indicative of extent of corrosion of a material of interest.

BACKGROUND

Sensitive material and equipment are often located in or exposed to corrosive environments. Corrosion damage to such material and equipment can cause serious operational difficulties and economic loss. In certain mission-critical and lethal-service situations, unexpected corrosion damage may lead to loss of life.

To avoid or mitigate adverse consequences of corrosion, repair or replacement of sensitive materials and equipment must occur before failure. However, unnecessary repairs or replacement can be costly. Accordingly, there has been a considerable amount of research into devices and procedures used to predict, detect and quantify corrosion. By detecting corrosion or the extent of corrosion, repairs or replacement of sensitive materials and equipment can be delayed until such detection indicates that sufficient corrosion has occurred to warrant maintenance.

One device proposed for the detection of corrosion is that of a thin metal film corrosion indicator. It has long been known that thin metal films exhibit distinctive changes in appearance and electrical properties when undergoing corrosion. See, e.g., Rohrback, G. H. & Roller, D., *Development of Thin Metal Film Corrosion Indicators,* Corrosion, Vol. 16, No. 8, August 1960, at 105–10. One common application is to deposit a thin metal film on a support with two contacts to the thin metal film. The thin metal film is often sensitized, e.g., artificially contaminated with a salt layer, to promote more even corrosion across the metal film. The two contacts may be fit to a hermetic seal feed-through connector. The hermetic seal feed-through connector ensures that the two contacts are not exposed to a corrosive environment. An electrical meter is then attached to the two contacts to detect resistance in the metal film. The electrical meter may be remote from the corrosion indicator and may monitor several corrosion indicator stations through the use of a station selector switch. Alternatively, the electrical meter may be portable and attached to each corrosion indicator individually for resistance measurement.

While such electrical corrosion indicators are useful, they are also cumbersome. It may not be practicable to maintain connection between the electrical meter and the corrosion indicator, e.g., the corrosion indicator may be desirably attached to a device in motion. In addition, limited accessability or spacial considerations may make it difficult to attach an electrical meter to the corrosion indicator in use.

For the reasons stated above, and for other reasons stated below which will become apparent to those skilled in the art upon reading and understanding the present specification, there is a need in the art for alternative apparatus and methods for detecting corrosion.

SUMMARY

One embodiment of the invention includes a corrosion sensor. The corrosion sensor includes a support, a power source contained on the support, a visual indicator contained on the support and coupled to the power source, and an electrode having an electrical resistance contained on the support and coupled to the power source and the visual indicator. Changes in the resistance of the electrode facilitate a display on the visual indicator. The display on the visual indicator includes either changes in color or changes in brightness. Such changes in color or brightness may be used to display an alpha-numeric message or other symbolic image in response to the change in resistance.

Another embodiment of the invention includes a method of monitoring corrosion of a material of interest. The method includes placing a corrosion sensor in an environment containing the material of interest. The corrosion sensor includes a support, a power source contained on the support, a visual indicator contained on the support and coupled to the power source, and an electrode having an electrical resistance contained on the support and coupled to the power source and the visual indicator. Changes in the resistance of the electrode facilitate a display on the visual indicator. The display on the visual indicator includes either changes in color or changes in brightness. The method further includes monitoring changes in the display on the visual indicator. The changes in the display on the visual indicator are indicative of corrosion of the material of interest.

A further embodiment of the invention includes a method of monitoring corrosion of a material of interest. The method includes placing a corrosion sensor in an environment containing the material of interest and directing an electromagnetic radiation source at the corrosion sensor. The electromagnetic radiation source activates a display on the corrosion sensor. The display is responsive to corrosion-induced changes in electrical resistance of the corrosion sensor. The method further includes monitoring changes in the display on the corrosion sensor. The changes in the display on the corrosion sensor are indicative of corrosion of the material of interest.

Other embodiments of the invention include corrosion sensors and methods of varying scope.

DESCRIPTION OF THE EMBODIMENTS

In the following detailed description of the preferred embodiments, reference is made to the accompanying drawings which form a part hereof, and in which is shown by way of illustration specific embodiments in which the inventions may be practiced. These embodiments are described in sufficient detail to enable those skilled in the art to practice the invention, and it is to be understood that other embodiments may be utilized and that process or mechanical changes may be made without departing from the scope of the present invention. The following detailed description is, therefore, not to be taken in a limiting sense, and the scope of the present invention is defined only by the appended claims and equivalents thereof.

The invention includes visually indicating corrosion sensors for use in environments that are either corrosive in nature, or potentially corrosive, and their methods of use. The corrosion sensors produce a visual display indicative of corrosion or extent of corrosion experienced by the corrosion sensor. The corrosion sensors are self-contained and can be sized for placement and use in small enclosures or on moving platforms.

For an indication of corrosion of a material or equipment of interest, a corrosion sensor is placed in the environment containing the material or equipment of interest. For convenience, references to material of interest used hereafter will refer to both material of interest and equipment of interest. The corrosion sensor's visual display indicative of corrosion or extent of corrosion experienced by the corrosion sensor may likewise be indicative of corrosion or extent of corrosion of the material of interest. This is especially true when the corrosion sensor contains similar materials as found in the material of interest.

Figure 1:
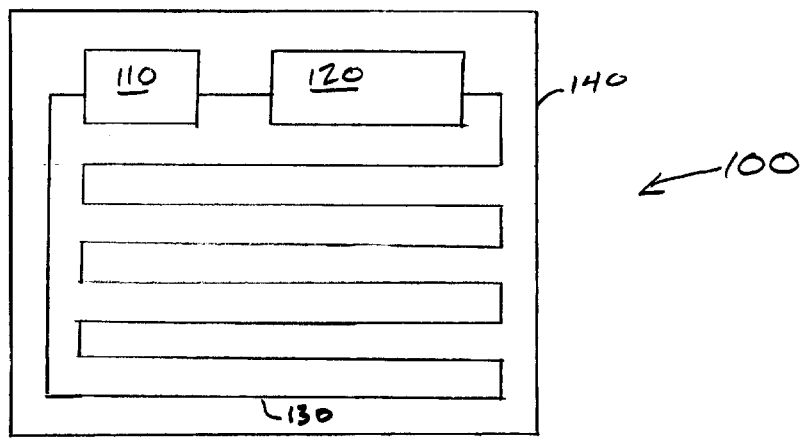
FIG. 1 is a corrosion sensor in accordance with one embodiment of the invention having a serial connection and serpentine electrode.

FIG. 1 depicts one embodiment of a visually indicating corrosion sensor 100. Corrosion sensor 100 contains a power source 110, a visual indicator 120 and an electrode 130 contained on a support 140. Power source 110 may include any supply source of a known voltage and current. In one embodiment, the supply source of power source 110 is a battery, e.g., a dry-cell battery, and may include multiple cells connected in series or parallel. In another embodiment, the supply. source of power source 110 is a photoelectric cell. The supply source of power source 110 may be removable and replaceable, and for purposes of this disclosure, the term power source includes receptacles adapted to receive a supply source, e.g., a battery compartment. Furthermore, power source 110 contained on support 140 may be imbedded within support 140 as a permanent power source, e.g., in a disposable corrosion sensor where the sensor is discarded in lieu of replacing the power source.

Power source 110 may further include regulator circuitry known to those skilled in the art to provide a constant voltage from the supply source across a wide range of operating conditions. Power source 110 preferably provides a substantially constant voltage across its useful life and normal operating conditions.

Visual indictor 120 is responsive to a voltage drop across visual indicator 120 or current flow through visual indicator 120, changing color and/or brightness depending on the magnitude of the voltage drop or current flow. Common examples include electrochromic materials, i.e., materials that change color in response to an applied voltage, and thermochromic materials, i.e., materials that change color when heated or cooled. Thermochromic materials are indirectly responsive to current flow through visual indicator 120 in that current flow through a conductor produces thermal losses, thus changing the temperature of visual indicator 120. One example of a thermochromic visual indicator is described in U.S. Pat. No. 4,006,414 issued Feb. 1, 1977 to Parker. One example of an electrochromic visual indicator is described in U.S. Pat. No. 4,225,216 issued Sep. 30, 1980 to Boyd et al. Other examples of materials suitable for visual indicator 120 include light-emitting diodes (LEDs), producing changing brightness levels over a range of current flows.

Changes in color and/or brightness may be utilized to produce alpha-numeric or other symbolic displays in visual indicator 120. As an example, visual indicator 120 may be configured to display the word "good" or "passed" above a predetermined level of current flow or voltage drop. As a further example, visual indicator 120 may be configured to display a bar of decreasing length in response to decreasing current flow or voltage drop. In this example, visual indicator 120 may further contain a graded scale along the length of the bar, e.g., 0–100 or bad/fair/good, to provide quantitative indication of extent of corrosion.

Electrode 130 is coupled on one end to a first terminal of power source 110 and on the other end to a first terminal of visual indicator 120. Power source 110 and visual indicator 120 are then coupled to each other via the remaining terminals to complete a circuit through power source 110, visual indicator 120 and electrode 130. Current may flow clockwise from power source 110, through visual indicator 120, through electrode 130 and back to power source 110. Alternatively, current in corrosion sensor 100 may flow counterclockwise. The direction of current flow is inconsequential. In addition, electrode 130 may be coupled between power source 110 and visual indicator 120.

While corrosion sensor 100 is depicted to have power source 110, visual indicator 120 and electrode 130 in series, such is not required. Visual indicator 120 and electrode 130 could be coupled to power source 110 in parallel, but the series connection is believed to be a more efficient use of power source 110. Furthermore, while electrode 130 of corrosion sensor 100 in FIG. 1 is depicted in a serpentine pattern, electrode 130 can take on any shape or pattern. In addition, a first portion of electrode 130 may overlie or underlie remaining portions of electrode 130, as long as the first portion is insulated from the remaining portions such as by imbedding the first portion in the support 140.

Figure 2A:
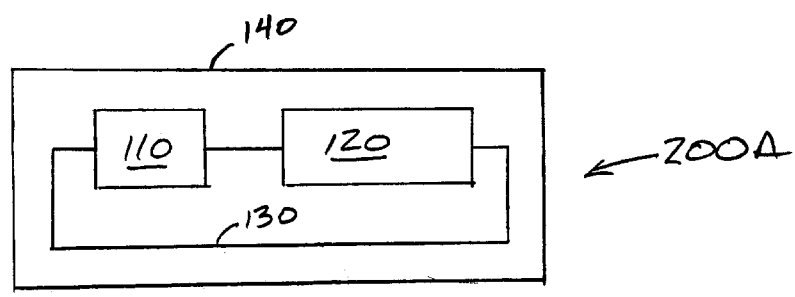
FIG. 2A is a corrosion sensor in accordance with one embodiment of the invention having a serial connection and a simple loop electrode.
Figure 2B:
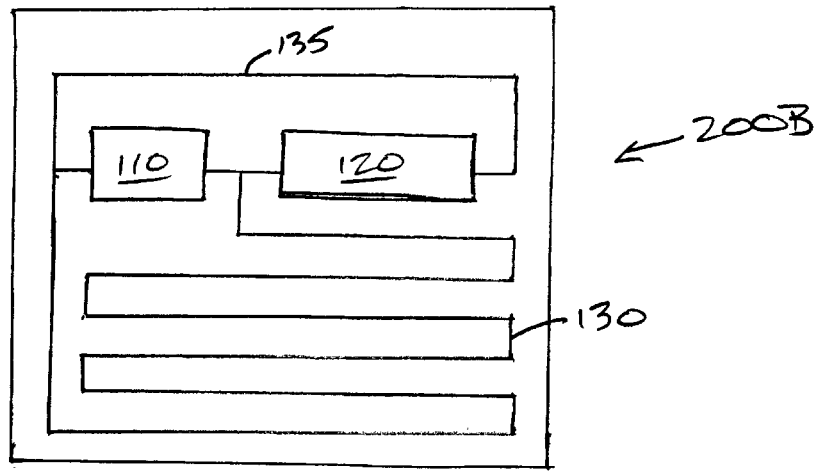
FIG. 2B is a corrosion sensor in accordance with one embodiment of the invention having a parallel connection.

FIG. 2A shows an alternate embodiment of a corrosion sensor 200A where electrode 130 forms a simple loop from visual indicator 120 to power source 110. Other circuit loops will be readily apparent to those skilled in the art. FIG. 2B shows an alternate embodiment of a corrosion sensor 200B where visual indicator 120 and electrode 130 are connected in parallel. Corrosion sensor 200B further includes a connection 135, thus having a first current path containing power source 110 and visual indicator 120, and a second current path containing power source 110 and electrode 130.

Support 140 is generally an insulative material. As an example, support 140 may be glass or plastic. Support 140 should be resistant to corrosion in the environment where corrosion sensor 100 is to be employed. Furthermore, support 140 should not promote corrosion of electrode 130, either spontaneously through outgassing of corrosive impurities or through the production of corrosive by-products in conjunction with exposure to the environment. Support 140 may encapsulate power supply 110 and visual indicator 120 to protect them from the environment. In any case, power supply 110 and visual indicator 120 should be either protected from the environment, such as applying a protective coating or providing a hermetic seal, or be otherwise resistant to corrosive damage. However, at least a portion of electrode 130 must be exposed to the environment.

Corrosion sensor 100 functions in response to physical changes in electrode 130 induced by corrosive attack. Electrical resistance in a conductor is inversely proportional to its effective cross-sectional area and directly proportional to its length. For a conductor having a constant cross-sectional area across its entire length, effective cross-sectional area equals its actual cross-sectional area. For a conductor having varying cross-sectional areas across its length, effective cross-sectional area will be between its minimum and maximum cross-sectional areas.

Electrode 130 has an effective cross-sectional area and a length as a conductor. As corrosion takes place in electrode 130, its effective cross-sectional area decreases causing an increase in resistance. The length of electrode 130 can be assumed to be substantially constant despite corrosion. As electrode 130 increases resistance to current flow, visual indicator 120 will experience a reduced voltage drop and a reduced current flow when connected in series with electrode 130, thus producing a distinctive color or brightness indicative of such a reduced voltage drop or current flow. Alternatively, if electrode 130 and visual indicator 120 are connected in parallel, increases in resistance of electrode 130 will lead to an increased voltage drop and increased current flow for visual indicator 120. Visual indicator 120 will likewise produce a distinctive color or brightness indicative of such an increased voltage drop or current flow.

Electrode 130 may be of any conductive material susceptible to corrosion. Electrode 130 is preferably a metal or metal alloy. Common examples include materials found throughout industry, including, without limitation, iron, aluminum, manganese, copper, carbon steel, silver, cobalt and molybdenum, as well as alloys containing one or more of these materials. Any corrosion experienced by electrode 130 may be indicative of corrosion of surrounding materials. Thus, corrosion experienced by electrode 130 may be indicative of corrosion experienced by the material of interest when exposed to the same environment. In one embodiment, electrode 130 contains the same material as the material of interest. As but one example, where the equipment of interest is a carbon steel support structure, electrode 130 may contain carbon steel.

Electrode 130 is applied to a surface of support 140 to produce a thin film. Electrode 130 may be applied in any manner. As one example, electrode 130 may contain a metal foil attached to support 140 using a contact adhesive or cement. As another example, electrode 130 may be vacuum deposited on support 140. As a further example, electrode 130 may be sputter deposited on support 140. As a still further example, electrode 130 may be deposited on support 140 through chemical-vapor deposition. As yet another example, electrode 130 may be deposited on support 140 through laser ablation.

Electrode 130 has a length substantially equal to the length of the current path along electrode 130 from visual indicator 120 to power source 110, a width measured along the surface of support 140 and normal to the current path of electrode 130, and a thickness measured normal to the surface of support 140.

The length, width and thickness of electrode 130 can be adjusted as design choices, and are not herein limited. For a credit-card sized corrosion sensor, typical values of length may range from about 5 to 20 inches, typical values of width may range from about 0.0125 to 0.5 inches, and typical values of thickness may range from about 0.0001 mils to 1 mil. Increasing the length will tend to increase initial resistance values while increasing width and thickness will tend to decrease initial resistance values. Furthermore, increasing width and thickness will tend to decrease the sensitivity of corrosion sensor 100, i.e, electrode 130 must experience higher levels of corrosion before a threshold resistance value is reached. It is noted that an electrode 130 having narrow widths will tend to be more sensitive to uneven corrosion in that localized corrosion may prematurely sever electrode 130, resulting in an open circuit. Increasing width will tend to minimize the likelihood of localized corrosion severing electrode 130 before the threshold resistance is reached.

Threshold resistance is defined as the absolute resistance value of electrode 130 that must be exceeded to indicate a maximum acceptable extent of corrosion. Indication of maximum acceptable extent of corrosion may include no color change in the thermochromic or electrochromic material of visual indicator 120, a color change across a defined percentage of visual indicator 120, lack of illumination of visual indicator 120, a defined brightness level of visual indicator 120, or display of an alpha-numeric message or other symbolic display.

Electrode 130 may be sensitized to promote more even or predictable corrosion. Sensitization may include the application of a salt layer over at least a portion of electrode 130. Sensitization may further include annealing the electrode 130 following application of the salt layer.

Figure 3:
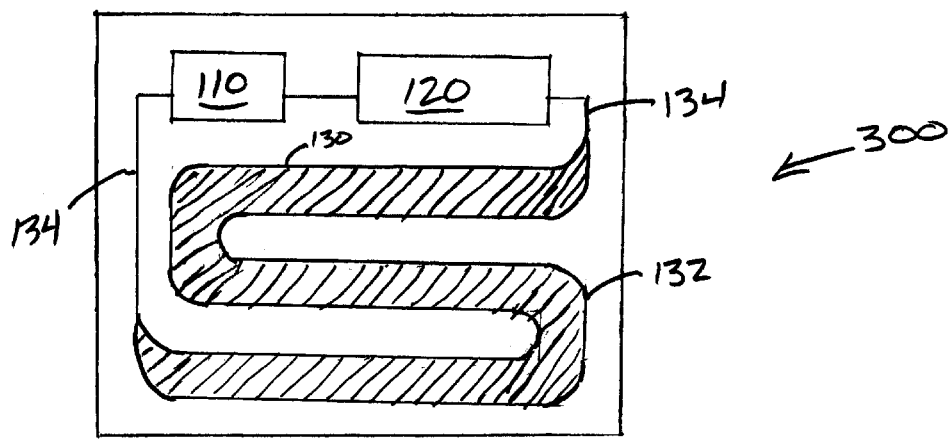
FIG. 3 is a corrosion sensor in accordance with one embodiment of the invention having a wide electrode portion.

FIG. 3 depicts another embodiment of a corrosion sensor 300. In this embodiment, electrode 130 includes a wide portion 132 and lead portions 134. Lead portions 134 provide coupling to power source 110 and visual indicator 120. Preferably, only wide portion 132 is sensitized. In addition, lead portions 134 are preferably protected from corrosive attack, although such protection is not necessary. Examples of protection of lead portions 134 include encapsulation of lead portions 134 in support 140, fabrication of lead portions 134 from a different material than wide portion 132 or application of a protective coating to lead portions 134. If lead portions 134 are of a different material than wide portion 132, consideration must be taken of the possibility of galvanic corrosion between the dissimilar materials. Lead portions 134 can be the same width, thickness and material as wide portion 132, such that they are simply an extension of wide portion 132.

Figure 4:
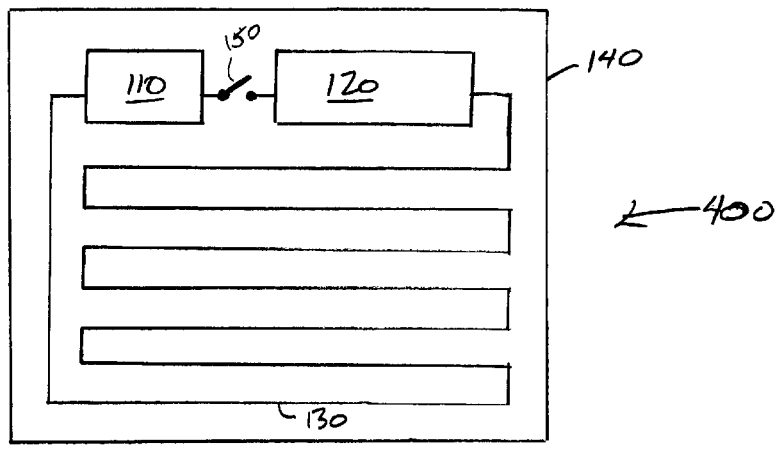
FIG. 4 is a corrosion sensor in accordance with one embodiment of the invention having a switch.

FIG. 4 depicts still another embodiment of a corrosion sensor 400. In this embodiment, corrosion sensor 400 further includes a switch 150. Switch 150 when open inhibits current flow from power source 110. Switch 150 can be used to conserve power of power source 110 between readings of visual indicator 120, or to simply inhibit display of any change of visual indicator 120 between readings. In normal practice, switch 150 would be closed at times when it is desired to read visual indicator 120 and open at all other times. Switch 150 can be of any type, but is preferably a sealed switch to avoid corrosive attack.

Figure 5:
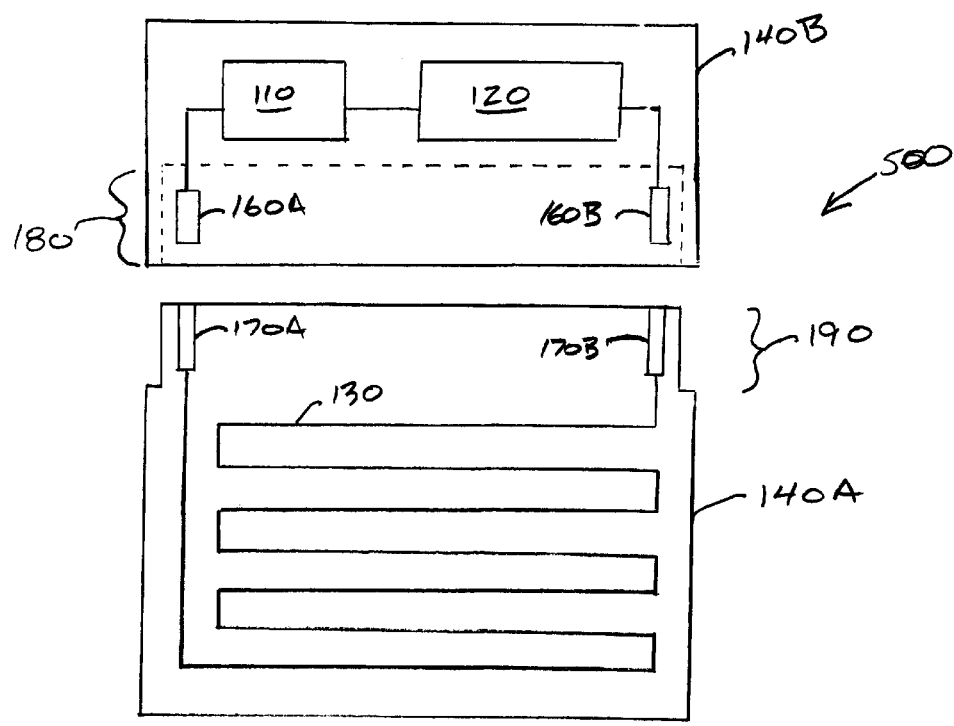
FIG. 5 is a corrosion sensor in accordance with one embodiment of the invention having a two-part support.

FIG. 5 depicts a further embodiment of a corrosion sensor 500. In the embodiment of FIG. 5, support 140 contains two parts 140A and 140B. Support 140A contains electrode 130 having a first contact 170A and a second contact 170B. Support 140A further contains a tab portion 190. Support 140B contains power source 110 and visual indicator 120. Support 140B further contains a slot portion 180, a first contact 160A to power source 110 and a second contact 160B to visual indicator 120. It should be readily apparent that if it is desired to have visual indicator 120 and electrode 130 in a parallel configuration, second contact 160B would be to power source 110.

Slot portion 180 of first part 140A is designed to mate with tab portion 190 of second part 140B such that contact 170A is in electrical communication with contact 160A and contact 170B is in electrical communication with contact 160B only when tab portion 190 is inserted into slot portion 180. Slot portion 180 should be hermetically sealed when tab portion 190 is inserted to avoid corrosive attack to contacts 160A and 160B during use. This may require a seal (not shown). The embodiment of FIG. 5 allows replacement and interchangeability of electrode 130 without discarding power source 110 and visual indicator 120.

Figure 6:
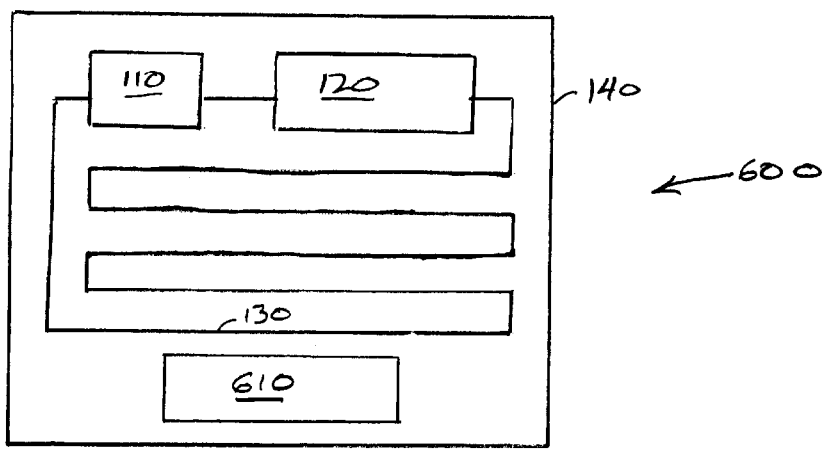
FIG. 6 is a corrosion sensor in accordance with one embodiment of the invention having a tracking device.

FIG. 6 depicts another embodiment of a corrosion sensor 600. In the embodiment of FIG. 6, corrosion sensor 600 contains a power source 110, a visual indicator 120, an electrode 130 and a tracking device 610 contained on a support 140. Tracking device 610 facilitates data management by providing visual or machine-readable tracking information about the corrosion sensor 600, e.g., one or more of identification number, location, age or other user-specified information. In one embodiment, tracking device 610 contains a bar code indicative of the tracking information and may be both visual and machine-readable. In another embodiment, tracking device 610 is an alpha-numeric label or other such visual information. In yet another embodiment, tracking device 610 is a magnetic stripe containing machine-readable information. In a further embodiment, tracking device 610 is an RF (radio frequency) transponder containing machine-readable information. As will be recognized, tracking device 610 may be imbedded in support 140 where the device operation permits. As an example, RF transponders may be read whether they are contained on the surface of support 140, or contained or imbedded within support 140. In a still further embodiment, tracking device 610 contains more than one format of tracking information.

Figure 7:
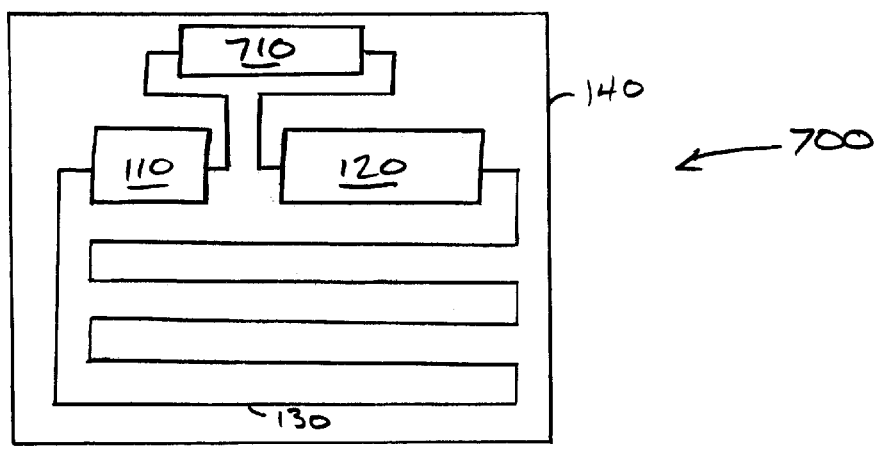
FIG. 7 is a corrosion sensor in accordance with one embodiment of the invention having a proximity sensor.

FIG. 7 depicts a further embodiment of a corrosion sensor 700. In the embodiment of FIG. 7, corrosion sensor 700 contains a power source 110, a visual indicator 120, an electrode 130 and a proximity sensor 710 contained on a support 140. Proximity sensor 710 is a switch (such as switch 150 of the embodiment of FIG. 4) that inhibits current flow from power source 110 to visual indicator 120 when "open" or not activated. Unlike switch 150, proximity sensor 710 automatically activates when a trigger (not shown) is positioned near proximity sensor 710, i.e., when the sensor is in proximity of the trigger. Proximity sensor 710 may supply its own power for operation or it may draw current from power source 110 in a separate circuit (not shown). Proximity sensor 710 may further be contained on the surface of support 140 or imbedded within support 140.

Examples of trigger mechanisms include RF transponders, such as might be contained in a security badge, or some other transmitter generating an electrical or magnetic field detectable by proximity sensor 710. The actual distance between the trigger and proximity sensor 710 necessary to activate proximity sensor 710 is dependent upon the design considerations of the proximity sensor 710 and the trigger. Proximity sensor 710 can be used to conserve power of power source 110 or to simply inhibit display of any change of visual indicator 120 when the trigger is not within the proximity of corrosion sensor 700. In practice, proximity sensor 710 may be used to induce display of visual indicator 120 only when designated or authorized personnel are present, as when the trigger is contained in a security badge.

In use, corrosion sensors of the invention may be placed in the environment with the material of interest. The corrosion sensor may be loose or simply resting in the environment, or it may be attached to some surface in the environment, including a surface of the material of interest. Support 140 may have a tab, punch hole or other means to suspend the corrosion sensor in the environment by hook, tie or other suitable means. The visual indicator of the corrosion sensor provides a display indicative of the resistance value of the electrode, and thus the extent of corrosion of the electrode. The visual indicator provides the display either through the continuous current flow through the power source/visual indicator/electrode circuit, or upon closing a switch to complete a circuit between the power source, visual indicator and electrode.

When the power source of the corrosion sensor is a photoelectric cell current flow can be induced by directing an electromagnetic radiation source at the corrosion sensor, and thus the power source, where the electromagnetic radiation source emits one or more wavelengths capable of generating current in the photoelectric cell. In one embodiment, the photoelectric cell is responsive to visible light and the electromagnetic radiation source is a flashlight. This application is particularly useful in remote locations or small enclosures where it desirable to avoid replacement of power sources or difficult to physically manipulate a switch. A user has the capacity to shine a flashlight on the corrosion sensor, thus inducing current flow in the photoelectric cell and powering the display of the corrosion sensor.

The characteristics of the corrosion sensors described herein allow attachment to moving platforms, such as a rotating shaft or oscillating member. In such applications, a strobe light might be utilized to seemingly stop the motion of the corrosion sensor to facilitate reading of the visual indicator by adjusting the frequency of the strobe to be a multiple of the frequency of the moving platform. Where the power source of the corrosion sensor is a photoelectric cell, the strobe light can also be used to generate current in the photoelectric cell to activate the visual indicator. Although this application may make a manual switch impractical for conserving the power source between readings where the power source is other than a photoelectric cell, a proximity sensor may be substituted for the manual switch. Again, a strobe light might be utilized to facilitate reading of the visual indicator.

In the various embodiments, the parameters of length, width and thickness of the electrode, as well as the voltage drop and current rating of the power source, are desirably chosen such that a distinctive display is produced on the visual indicator at a time when the extent of corrosion is indicative of some known extent of corrosion of the material of interest, e.g., a level of corrosion where maintenance is desirable.

CONCLUSION

Corrosion sensors and methods of their use for monitoring corrosion of a material of interest have been described. The corrosion sensors are adapted to be placed in the environment containing the material of interest during the period when corrosion is taking place. The corrosion sensors include a power source, a visual indicator and an electrode contained on a support. Changes in the electrical resistance of the electrode facilitate a display on the visual indicator including changes in color or brightness. Some corrosion sensors have power sources activated by directing a light source or other electromagnetic radiation source at the corrosion sensor. Some corrosion sensors have visual indicators containing thermochromic or electrochromic materials that are responsive to changes in voltage drop or current flow across the visual indicator. Some corrosion sensors have tracking devices to provide tracking information about the corrosion sensor. Some corrosion sensors have proximity sensors to inhibit the display on the visual indicator when not in proximity of a trigger.

Although specific embodiments have been illustrated and described herein, it will be appreciated by those of ordinary skill in the art that any arrangement which is calculated to achieve the same purpose may be substituted for the specific embodiments shown. Many adaptations of the invention will be apparent to those of ordinary skill in the art. Individual aspects of the example embodiments may be combined, e.g., a switch may be combined with an embodiment having a parallel connection, a proximity sensor may be combined with an embodiment having a tracking device, a tracking device or proximity sensor may be combined with an embodiment having a two-part support, and more. Accordingly, this application is intended to cover any adaptations or variations of the invention. It is manifestly intended that this invention be limited only by the following claims and equivalents thereof.

What is claimed is:

1. A corrosion sensor, comprising:

a support;

a power source contained on the support;

a visual indicator contained on the support and coupled to the power source; and a corrodable electrode having an electrical resistance contained on the support and coupled to the power source and the visual indicator;

wherein changes in the resistance due to corrosion of the electrode facilitate a display on the visual indicator selected from the group consisting of changes in color and changes in brightness.

2. The corrosion sensor of claim 1, wherein the power source comprises a supply source selected from the group consisting of a battery and a photoelectric cell.

3. The corrosion sensor of claim 1, wherein the visual indicator comprises a material selected from the group consisting of the thermochromic materials and electrochromic materials.

4. The corrosion sensor of claim 1, wherein the power source, visual indicator and electrode are coupled in series.

5. The corrosion sensor of claim 1, wherein the electrode comprises a conductive film comprising a material selected from the group consisting of metals and metal alloys.

6. The corrosion sensor of claim 1, wherein the corrodable electrode comprises a conductive film comprising a material selected from the group consisting of iron, aluminum, manganese, copper, carbon steel, silver, cobalt, molybdenum, and alloys of iron, aluminum, manganese, copper, silver, cobalt and molybdenum.

7. The corrosion sensor of claim 1, wherein at least a portion of the corrodable electrode is sensitized.

8. The corrosion sensor of claim 1, wherein at least a portion of the corrodable electrode has a width of approximately 0.0125 to 0.5 inches.

9. The corrosion sensor of claim 1, wherein at least a portion of the corrodable electrode has a thickness of approximately 0.0001 mils to 1 mil.

10. The corrosion sensor of claim 1, further comprising a switch having an open and a closed position and coupled to the power source, wherein the switch is adapted to inhibit current flow from the power source when in the open position.

11. The corrosion sensor of claim 1 wherein the visual indicator indicates the amount of corrosion of the corrodable electrode.

12. A method of monitoring corrosion of a material of interest, comprising:

placing a corrosion sensor in an environment containing the material of interest, wherein the corrosion sensor comprises:

a support;

a power source contained on the support;

a visual indicator contained on the support and coupled to the power source; and a corrodable electrode having an electrical resistance contained on the support and coupled to the power source and the visual indicator;

wherein changes in the resistance due to corrosion of the electrode facilitate a display on the visual indicator selected from the group consisting of changes in color and changes in brightness; and monitoring changes in the display on the visual indicator, wherein the changes in the display on the visual indicator are indicative of corrosion of the material of interest.

13. The method of monitoring corrosion of a material of interest of claim 12 wherein the visual indicator indicates the amount of corrosion of the corrodable electrode.

14. A corrosion sensor, comprising:

a support;

a power source contained on the support, wherein the power source comprises a supply source selected from the group consisting of a battery and a photoelectric cell;

a visual indicator contained on the support and coupled to the power source, wherein the visual indicator comprises a material selected from the group consisting of thermochromic materials and electrochromic materials; and a corrodable electrode having an electrical resistance contained on the support and coupled to the power source and the visual indicator, wherein the corrodable electrode comprises a material selected from the group consisting of metals and metal alloys;

wherein changes in the resistance due to corrosion of the electrode facilitate a display on the visual indicator selected from the group consisting of changes in color and changes in brightness.

15. The corrosion sensor of claim 14 wherein the visual indicator indicates the amount of corrosion of the corrodable electrode.

16. A method of monitoring corrosion of a material of interest, comprising:

placing a corrosion sensor in an environment containing the material of interest, wherein the corrosion sensor comprises:

a support;

a power source contained on the support, wherein the power source comprises a supply source selected from the group consisting of a battery and a photoelectric cell;

a visual indicator contained on the support and coupled to the power source, wherein the visual indicator comprises a material selected from the group consisting of thermochromic materials and electrochromic materials; and a corrodable electrode having an electrical resistance contained on the support and coupled to the power source and the visual indicator, wherein the corrodable electrode comprises a material selected from the group consisting of metals and metal alloys;

wherein changes in the resistance due to corrosion of the corrodable electrode facilitate a display on the visual indicator selected from the group consisting of changes in color and changes in brightness; and monitoring changes in the display on the visual indicator, wherein the changes in the display on the visual indicator are indicative of corrosion of the material of interest.

17. A method for sensing corrosion comprising:

passing current through a corrodable electrode; and visually indicating the amount of corrosion of the corrodable electrode based on the amount of current passing through the corrodable electrode.

18. A corrosion sensor comprising:

a power source;

a visual indicator;

a corrodable electrode, pluggably connectable to the power source and the visual indicator wherein the visual indicator indicates the amount of corrosion of the electrode in response to the change in the resistance of the corrodable electrode due to corrosion.

* * * * *